United States Patent
Giampietro et al.

(10) Patent No.: US 9,518,019 B2
(45) Date of Patent: Dec. 13, 2016

(54) PROCESS FOR THE PREPARATION OF 4-AMINO-5-FLUORO-3-CHLORO-6-(SUBSTITUTED)PICOLINATES

(71) Applicant: Dow AgroSciences LLC, Indianapolis, IN (US)

(72) Inventors: Natalie C. Giampietro, Carmel, IN (US); James M. Renga, Spokane, WA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/040,577

(22) Filed: Feb. 10, 2016

(65) Prior Publication Data
US 2016/0159742 A1    Jun. 9, 2016

Related U.S. Application Data

(62) Division of application No. 14/104,127, filed on Dec. 12, 2013, now Pat. No. 9,260,392.

(60) Provisional application No. 61/736,841, filed on Dec. 13, 2012.

(51) Int. Cl.
| | |
|---|---|
| *C07D 213/79* | (2006.01) |
| *C07D 213/803* | (2006.01) |
| *C07C 251/12* | (2006.01) |

(52) U.S. Cl.
CPC ........... *C07D 213/79* (2013.01); *C07C 251/12* (2013.01); *C07D 213/803* (2013.01)

(58) Field of Classification Search
None
See application file for complete search history.

(56) References Cited

U.S. PATENT DOCUMENTS

| | | | | |
|---|---|---|---|---|
| 3,830,822 | A * | 8/1974 | Barlow | A01N 43/40 504/155 |
| 6,784,137 | B2 * | 8/2004 | Balko | A01N 43/40 504/244 |
| 7,314,849 | B2 * | 1/2008 | Balko | A01N 43/40 504/244 |
| 7,432,227 | B2 * | 10/2008 | Balko | C07D 213/79 504/244 |

OTHER PUBLICATIONS

Akimoto et al, Chemistry Letters (1977), (9), pp. 1061-1064.*

* cited by examiner

*Primary Examiner* — Zinna Northington Davis
(74) *Attorney, Agent, or Firm* — Michael R. Asam

(57) ABSTRACT

4-Amino-5-fluoro-3-chloro-6-(substituted)picolinates are prepared from trifluoroacetic acid, p-methoxyaniline, a $C_1$-$C_4$ alkyl propiolate and a substituted methylene amine by a series of steps.

2 Claims, No Drawings

PROCESS FOR THE PREPARATION OF 4-AMINO-5-FLUORO-3-CHLORO-6-(SUBSTITUTED)PICOLINATES

CROSS REFERENCE TO RELATED APPLICATIONS

This application is a Divisional of U.S. patent Ser. No. 14/104,127, filed on Dec. 12, 2013, and claims the benefit of U.S. Provisional Patent Application Ser. No. 61/736,841 filed Dec. 13, 2012, the disclosure of which is expressly incorporated herein by reference.

FIELD

Provided herein are processes for the preparation of 4-amino-5-fluoro-3-chloro-6-(substituted)picolinates. More particularly, provided herein are processes for the preparation of 4-amino-5-fluoro-3-chloro-6-(substituted)picolinates from a non-pyridine source.

BACKGROUND

U.S. Pat. Nos. 6,784,137 B2 and 7,314,849 B2 describe inter alia certain 4-amino-5-fluoro-3-chloro-6-(aryl)picolinate compounds and their use as herbicides. U.S. Pat. No. 7,432,227 B2 describes inter alia certain 4-amino-5-fluoro-3-chloro-6-(alkyl)picolinate compounds and their use as herbicides. Each of these patents describes the manufacture of 4-amino-5-fluoro-3-chloropicolinate starting materials by fluorination of the corresponding 5-unsubstituted pyridines with 1-(chloromethyl)-4-fluoro-1,4-diazoniabicyclo[2.2.2]octane bis(tetrafluoroborate). Each of these patents also describes the manufacture of 6-(aryl)-4-aminopicolinates from coupling reactions involving picolines having either a facile leaving group or a metal derivative in the 6-position of the picoline ring. It would be advantageous to produce 4-amino-5-fluoro-3-chloro-6-(substituted)picolinates without having to rely on metal assisted couplings. It would be advantageous to produce 4-amino-5-fluoro-3-chloro-6-(substituted)picolinates efficiently and in high yield from a non-pyridine source. It would also be advantageous to produce 4-amino-5-fluoro-3-chloro-6-(substituted)picolinates without having to rely on direct fluorination of the 5-position of the pyridine ring with an expensive fluorinating agent like 1-(chloromethyl)-4-fluoro-1,4-diazoniabicyclo[2.2.2]octane bis(tetrafluoroborate).

SUMMARY

Provided herein are processes for the preparation of 4-amino-5-fluoro-3-chloro-6-(substituted)picolinates from a non-pyridine source without a metal assisted coupling and without fluorination with an expensive fluorinating agent like 1-(chloromethyl)-4-fluoro-1,4-diazoniabicyclo[2.2.2]octane bis(tetrafluoroborate). More particularly, provided herein are processes for the preparation of a 4-amino-5-fluoro-3-chloro-6-(substituted)picolinate of the Formula I

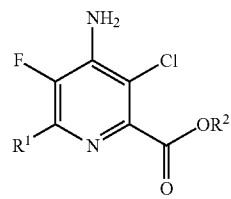

wherein
R$^1$ represents C$_1$-C$_4$ alkyl, cyclopropyl, C$_2$-C$_4$ alkenyl or phenyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy, and
R$^2$ represents C$_1$-C$_4$ alkyl,
which comprises the following steps:
a) contacting trifluoroacetic acid with p-methoxyaniline in the presence of a triarylphosphine and a trialkylamine base in carbon tetrachloride solvent to produce an acetimidoyl chloride of Formula A

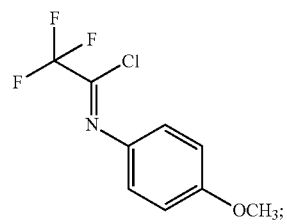

b) contacting the acetimidoyl chloride of Formula A with a C$_1$-C$_4$ alkyl propiolate (Formula B)

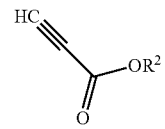

wherein R$^2$ is as previously defined,
in the presence of copper (I) iodide, an alkali metal iodide and an alkali metal phosphate in a polar aprotic solvent to produce an (imino)pent-2-ynoate of Formula C

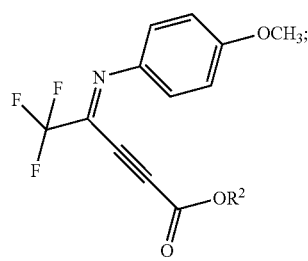

c) cyclizing the (imino)pent-2-ynoate of Formula C with an amine of Formula D

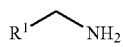

D wherein R¹ is as previously defined,
in the presence of an inorganic alkali metal base in a polar aprotic solvent at temperature from about ambient to about 100° C. to produce an alkyl 4-amino-5-fluoro-6-(substituted)-picolinate of Formula E

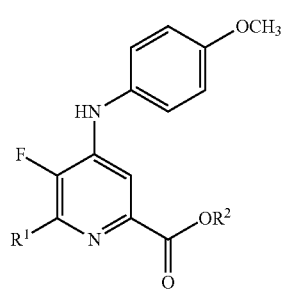

E wherein R¹ and R² are as previously defined; and
d) halogenating and deprotecting the alkyl 4-amino-5-fluoro-6-(substituted)picolinate of Formula E with 1,3-dichloro-5,5-dimethylimidazolidine-2,4-dione (Formula F)

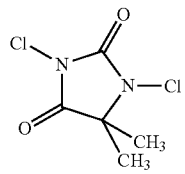

F in the presence of a mineral acid in a polar solvent to produce the 4-amino-5-fluoro-3-chloro-6-(substituted)picolinate of the Formula I.

Provided herein are also processes for the preparation of a 4-amino-5-fluoro-3-chloro-6-(substituted)picolinate of the Formula I

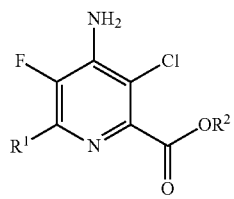

I wherein
R¹ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and
R² represents $C_1$-$C_4$ alkyl,
which comprises halogenating and deprotecting an alkyl 4-amino-5-fluoro-6-(substituted)-picolinate of Formula E

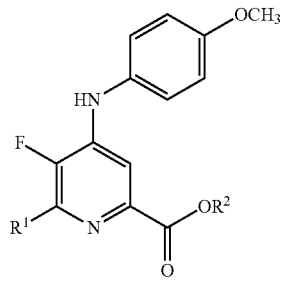

E wherein R¹ and R² are as previously defined,
with 1,3-dichloro-5,5-dimethylimidazolidine-2,4-dione (Formula F)

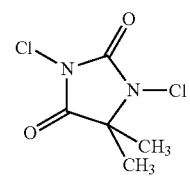

F in the presence of a mineral acid in a polar solvent to produce the 4-amino-5-fluoro-3-chloro-6-(substituted)picolinate of the Formula I.

Another embodiment is a compound of Formula E

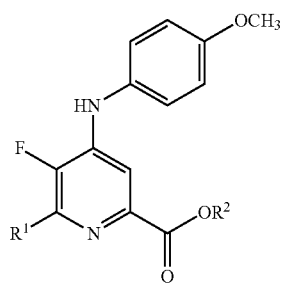

E wherein
R¹ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and
R² represents $C_1$-$C_4$ alkyl.
Another embodiment is a compound of Formula C

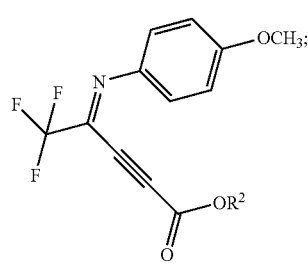

C wherein
R² represents C₁-C₄ alkyl.

Another embodiment is a compound of Formula G

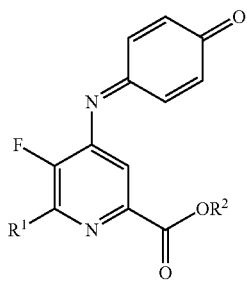

wherein
R¹ represents C₁-C₄ alkyl, cyclopropyl, C₂-C₄ alkenyl or phenyl substituted with from 1 to 4 substituents independently selected from halogen, C₁-C₄ alkyl, C₁-C₄ haloalkyl, C₁-C₄ alkoxy or C₁-C₄ haloalkoxy, and
R² represents C₁-C₄ alkyl.

DETAILED DESCRIPTION

The term alkyl and derivative terms such as alkoxy, as used herein refer to straight chain or branched chain groups. Typical alkyl groups are methyl, ethyl, propyl, 1-methylethyl, butyl, 1,1-dimethylethyl and 1-methylpropyl. Methyl and ethyl are often preferred.

Unless specifically limited otherwise, the term "halogen," as well as derivative terms such as "halo," refers to fluorine, chlorine, bromine and iodine.

The phenyl groups substituted with from 1 to 4 substituents independently selected from halogen, C₁-C₄ alkyl, C₁-C₄ haloalkyl, C₁-C₄ alkoxy or C₁-C₄ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

Alkyl 4-amino-5-fluoro-3-chloro-6-(substituted)picolinates are prepared from trifluoroacetic acid, p-methoxyaniline, a C₁-C₄ alkyl propiolate and a substituted methylene amine by a series of steps.

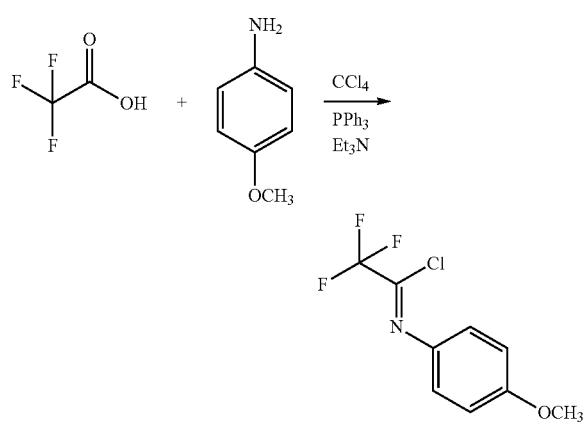

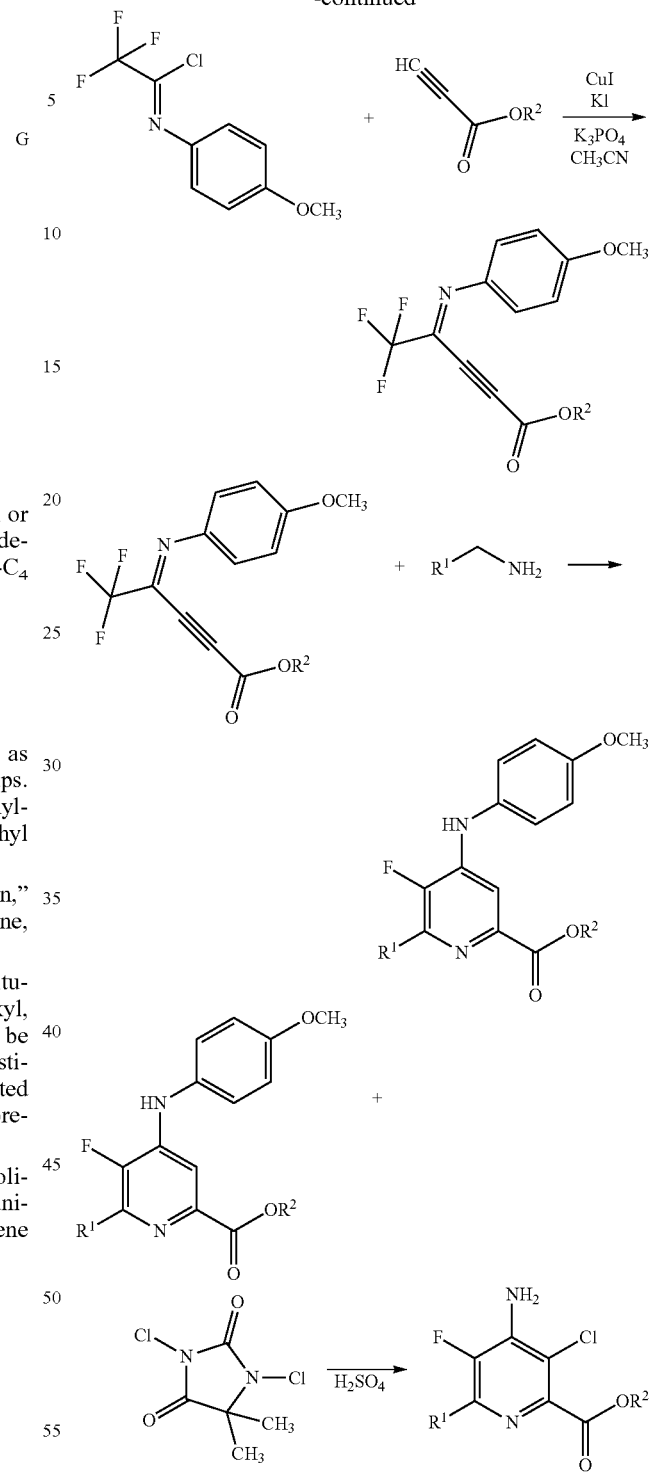

In the initial step, trifluoroacetic acid is reacted with p-methoxyaniline and carbon tetrachloride in the presence of a triarylphosphine and a trialkylamine base to produce 2,2,2-trifluoro-N-(4-methoxyphenyl)acetimidoyl chloride. While one equivalent of p-methoxyaniline is required for each equivalent of trifluoroacetic acid, it is often convenient to use an excess of the aniline, typically a 10 to 20% excess. A similar excess of trialkylamine base is also preferred. It is often convenient to use a much larger excess of triarylphosphine, typically in the range of a 2 to 4 fold excess. Carbon tetrachloride, while serving as a reactant, is also conveniently used as a solvent for the initial reaction. The reaction is exothermic and it is convenient to control the exotherm by external cooling and the controlled addition of a carbon tetrachloride solution of p-methoxyaniline to a mixture of trifluoroacetic acid, trialkylamine and triarylphosphine in carbon tetrachloride. After the initial exotherm subsides, the reaction mixture is generally heated to reflux until the conversion is complete.

In a typical reaction, a mixture of about 3 equivalents of triphenylphosphine and trifluoroacetic acid in carbon tetrachloride is cooled to about 0° C. in an ice bath and a 20% excess of triethylamine is added. With continued cooling, about a 20% excess of p-methoxyaniline in carbon tetrachloride is slowly added. After completion of the addition, the mixture is heated to about 70° C. for several hours. After cooling, the reaction mixture is extracted with hexane and the solvent is evaporated to provide crude 2,2,2-trifluoro-N-(4-methoxyphenyl)acetimidoyl chloride.

In the second step, the 2,2,2-trifluoro-N-(4-methoxyphenyl)acetimidoyl chloride is coupled with a $C_1$-$C_4$ alkyl propiolate in the presence of copper (I) iodide, an alkali metal iodide and an alkali metal phosphate in a polar aprotic solvent to produce a $C_1$-$C_4$ alkyl 5,5,5-trifluoro-4-((4-methoxyphenyl)imino)pent-2-ynoate. While one equivalent of $C_1$-$C_4$ alkyl propiolate is required for each equivalent of acetimidoyl chloride, it is often convenient to use an excess of the propiolate, typically a 10 to 20% excess. Similarly, a 10 to 20% molar excess of alkali metal iodide and alkali metal phosphate are generally preferred. While the reaction is catalytic in copper (I) iodide, usually about 0.1 to about 0.3 equivalents are employed. The coupling reaction is conducted in a polar aprotic solvent at a temperature from about 40° C. to about 100° C. Preferred polar aprotic solvents include ethers like tetrahydrofuran, esters like ethyl acetate, nitriles like acetonitrile, amides like N,N-dimethylformamide and N-methyl pyrrolidinone and sulfoxides like dimethyl sulfoxide. Anhydrous solvents are preferred with anhydrous acetonitrile being especially preferred.

In a typical reaction, 2,2,2-trifluoro-N-(4-methoxyphenyl)acetimidoyl chloride and a slight excess of methyl propiolate are mixed with about 0.3 equivalents of copper (I) iodide and slight excesses of potassium phosphate and potassium iodide in anhydrous acetonitrile. The mixture is heated at about 60° C. under a nitrogen atmosphere until the reaction is complete. After cooling, an extraction solvent like a halogenated hydrocarbon is added to the mixture along with water. The organic layer is recovered, washed with brine and dried. The solvent is evaporated to provide crude methyl 5,5,5-trifluoro-4-((4-methoxyphenyl)imino)pent-2-ynoate.

In the cyclization reaction, the 5,5,5-trifluoro-4-((4-methoxyphenyl)imino)pent-2-ynoate is reacted with a methylene amine substituted with an alkyl, cyclopropyl, alkenyl or (substituted)phenyl group in the presence of an inorganic alkali metal base in a polar aprotic solvent to produce an alkyl 4-(4-methoxyphenylamino)-5-fluoro-6-(substituted)picolinate. While one equivalent of substituted methylene amine is required for each equivalent of 5,5,5-trifluoro-4-((4-methoxyphenyl)imino)pent-2-ynoate, it is often convenient to use an excess of the methylene amine, typically a 2 to 4 fold excess. Suitable inorganic alkali metal bases include the lithium, sodium, potassium and cesium salts of hydroxides, carbonates and phosphates. Cesium carbonate is particularly preferred. In general, it is convenient to use a 2 to 4 fold excess of the inorganic alkali metal base. Preferred polar aprotic solvents include ethers like tetrahydrofuran, esters like ethyl acetate, nitriles like acetonitrile, amides like N,N-dimethylformamide and N-methylpyrrolidinone and sulfoxides like dimethyl sulfoxide. Anhydrous solvents are preferred with anhydrous tetrahydrofuran and dimethyl sulfoxide being especially preferred. The reaction is typically conducted at a temperature from about ambient to about 100° C.

In a typical reaction, methyl 5,5,5-trifluoro-4-((4-methoxyphenyl)imino)pent-2-ynoate is mixed with about a 2.5 to 3 fold excess of 4-chlorobenzyl amine and about a 2.5 to 3 fold excess of cesium carbonate in anhydrous tetrahydrofuran. The mixture is heated at about 80° C. until the reaction is complete. After cooling, an extraction solvent like a halogenated hydrocarbon is added to the mixture along with water. The organic layer is recovered, washed with brine and dried. The solvent is evaporated to provide crude methyl 4-(4-methoxyphenylamino)-5-fluoro-6-(4-chlorophenyl)picolinate.

The final step involves both the chlorination and the deprotection of the amino group by removal of the 4-methoxyphenyl substituent. An alkyl 4-(4-methoxyphenylamino)-5-fluoro-6-(substituted)picolinate is reacted with 1,3-dichloro-5,5-dimethylimidazolidine-2,4-dione in the presence of a mineral acid in a polar solvent at a temperature from about ambient to about 100° C. to produce an alkyl 4-amino-5-fluoro-3-chloro-6-(substituted)picolinate. While one equivalent of 1,3-dichloro-5,5-dimethylimidazolidine-2,4-dione is required for each equivalent of alkyl 4-(4-methoxyphenylamino)-5-fluoro-6-(4-chlorophenyl)picolinate, it is often convenient to use an excess of the 1,3-dichloro-5,5-dimethylimidazolidine-2,4-dione, typically a 2 to 4 fold excess. Suitable mineral acids include sulfuric and phosphoric acids with sulfuric acid being preferred. The mineral acids are usually used as aqueous solutions. Approximately one equivalent of mineral acid is required but a 10 to 30% excess is preferred. The chlorination/deprotection is conveniently performed in a mixture of a polar solvent such as acetonitrile with water.

If the chlorination/deprotection reaction is performed in the absence of the mineral acid, an alkyl 4-((4-oxocyclohexa-2,5-dien-1-ylidene)amino)-5-fluoro-6-(substituted)picolinate (Formula G) is obtained without chlorination of the 3-position on the pyridine ring.

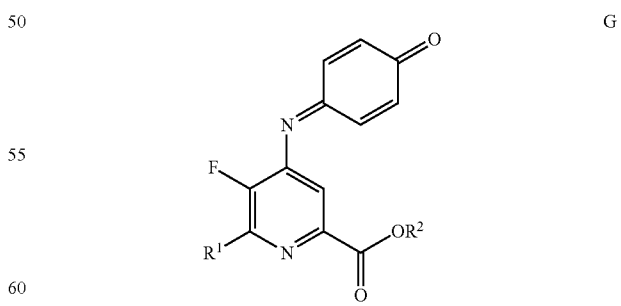

G

The alkyl 4-((4-oxocyclohexa-2,5-dien-1-ylidene)amino)-5-fluoro-6-(substituted)picolinate can be subsequently reacted with a mineral acid to deprotect the amino group and provide an alkyl 4-amino-5-fluoro-6-(substituted)picolinate (Formula H).

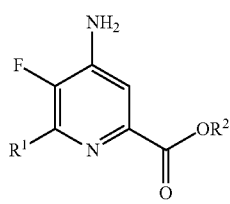

In a typical reaction accomplishing both chlorination and deprotection, methyl 4-(4-methoxyphenylamino)-5-fluoro-6-(4-chlorophenyl)picolinate is reacted with about two equivalents of 1,3-dichloro-5,5-dimethylimidazolidine-2,4-dione in the presence of a 1 M (molar) solution of sulfuric acid in a mixture of acetonitrile/water. The mixture is heated at reflux until the reaction is complete. The mixture is added to methylene chloride and the organic layer is separated, washed with brine and dried. The solvent is evaporated to provide crude methyl 4-amino-5-fluoro-3-chloro-6-(4-chlorophenyl)picolinate.

The products obtained by any of these processes, can be recovered by conventional means, such as evaporation or extraction, and can be purified by standard procedures, such as by distillation, crystallization or chromatography.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example 1

2,2,2-Trifluoro-N-(4-methoxyphenyl)acetimidoyl chloride

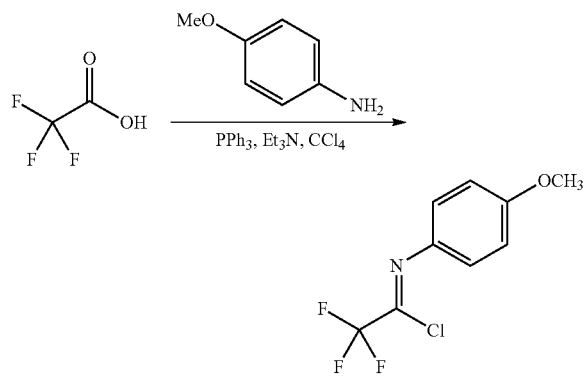

A mixture of triphenylphosphine (34.6 grams (g), 132.0 millimoles (mmol)), 2,2,2-trifluoroacetic acid (3.37 milliliters (mL), 44 mmol), triethylamine (7.38 mL, 53.0 mmol) and carbon tetrachloride (21.3 mL, 220.0 mmol) was magnetically stirred while cooled with an ice bath. After 10 minutes (min), p-methoxyaniline (6.53 g, 53.0 mmol) dissolved in carbon tetrachloride (21 mL, 220.0 mmol) was added slowly (exothermic). The ice bath was removed, and the reaction mixture was stirred at reflux for 4 hours (h). Upon cooling to room temperature, the reaction mixture was washed with hexane (3×100 mL). Solvent was removed using a rotary evaporator to give 9.8 g of an orange oil. Distillation gave 2,2,2-trifluoro-N-(4-methoxyphenyl)acetimidoyl chloride (9.31 g, 39.2 mmol, 89% yield) as a light yellow liquid: by 75-77° C./0.3 mmHg; $^1$H NMR (400 MHz, CDCl$_3$) δ 7.31 (m, 2H), 6.96 (m, 2H), 3.84 (s, 3H); $^{13}$C NMR (101 MHz, CDCl$_3$) δ 159.56 (s), 135.45 (s), 127.98 (q), 124.35 (s), 117.05 (q), 114.25 (s), 55.50 (s).

Example 2

Methyl 5,5,5-trifluoro-4-((4-methoxyphenyl)imino)pent-2-ynoate

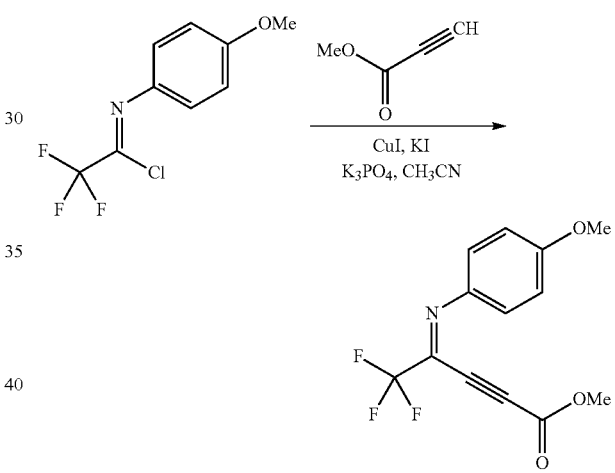

To a magnetically stirred solution of 2,2,2-trifluoro-N-(4-methoxyphenyl)-acetimidoyl chloride (2.376 g, 10.00 mmol) and methyl propiolate (1.009 g, 12.00 mmol) in anhydrous acetonitrile (CH$_3$CN; 20 mL) was added a ground-up mixture of copper(I) iodide (0.571 g, 3.00 mmol), potassium phosphate (2.55 g, 12.00 mmol) and potassium iodide (1.660 g, 10.00 mmol). After heating for 4 h at 60° C. under nitrogen, the reaction mixture was added to dichloromethane (CH$_2$Cl$_2$; 100 mL) and water (H$_2$O; 50 mL). The organic layer was washed with a saturated solution of sodium chloride (NaCl) and dried (magnesium sulfate (MgSO$_4$)), and the solvent was removed leaving 3.4 g of a dark brown oil. The material was passed through a plug of silica gel eluting with 5% ethyl acetate (EtOAc)/hexane to give methyl 5,5,5-trifluoro-4-((4-methoxyphenyl)imino)pent-2-ynoate (2.11 g, 7.40 mmol, 74.0% yield) as an orange oil: $^1$H NMR (400 MHz, CDCl$_3$) δ 7.54 (m, 2H), 6.97 (m, 2H), 3.86 (s, 3H), 3.85 (s, 3H); $^{13}$C NMR (101 MHz, CDCl$_3$) δ 161.11 (s), 152.43 (s), 138.87 (s), 131.88 (q), 125.46 (s), 118.70 (q), 114.33 (s), 86.82 (s), 73.95 (s), 55.59 (s), 53.50 (s); HRMS-ESI (m/z) [M+H]$^+$ calcd for $C_{17}H_{11}ClF_3NO$, 285.0613. found 285.0611.

Example 3

Methyl 6-(4-chlorophenyl)-5-fluoro-4-((4-methoxyphenyl)amino)picolinate

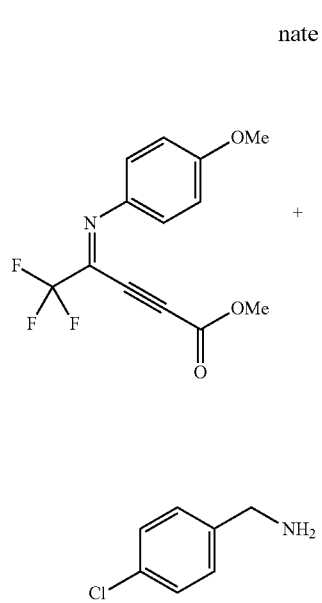

A magnetically stirred solution of methyl 5,5,5-trifluoro-4-(4-methoxyphenyl-imino)pent-2-ynoate (0.570 g, 2.0 mmol), p-chlorobenzylamine (0.850 g, 6.00 mmol) and cesium carbonate (1.629 g, 5.00 mmol) in anhydrous tetrahydrofuran (THF; 10 mL) was heated to 80° C. in a Discover CEM microwave for 4 h. Upon cobbling to room temperature, the reaction mixture was added to $CH_2Cl_2$ (50 mL) and $H_2O$ (50 mL). The organic layer was washed with a saturated solution of NaCl and dried ($MgSO_4$), and the solvent was removed leaving 1.3 g of a dark orange/brown oil. Preparative thin layer chromatography (TLC) on silica eluting with 20% EtOAc/hexane gave methyl 6-(4-chlorophenyl)-5-fluoro-4-((4-methoxyphenyl)amino)picolinate (0.31 g, 0.801 mmol, 40.1% yield) as an orange/yellow solid. Trituration with ether gave a white solid (0.145 g): mp 162-164° C.; $^1$H NMR (400 MHz, CDCl$_3$) δ 7.91 (dd, J=8.5, 1.5 Hz, 2H), 7.61 (d, J=6.0 Hz, 1H), 7.52-7.39 (m, 2H), 7.25-7.13 (m, 2H), 7.07-6.91 (m, 2H), 6.30 (d, J=3.6 Hz, 1H), 3.92 (s, 3H), 3.85 (s, 3H); $^{19}$F NMR (376 MHz, CDCl$_3$) δ -133.26; HRMS-ESI (m/z) [M+H]$^+$ calcd for $C_{20}H_{16}ClFN_2O_3$, 386.0833; found 386.0834.

Example 4

Methyl 4-amino-3-chloro-6-(4-chlorophenyl)-5-fluoropicolinate

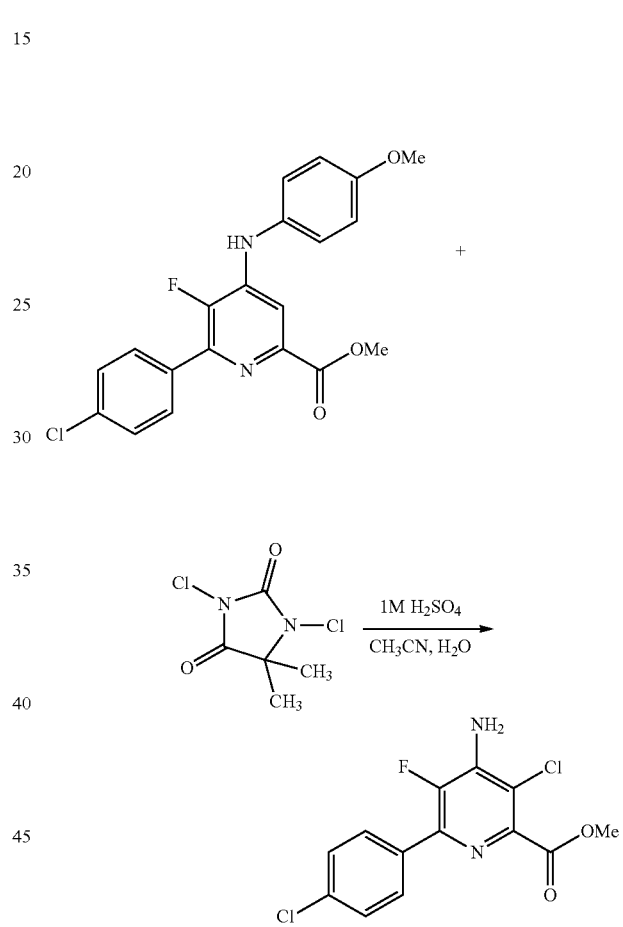

To a mixture of methyl 6-(4-chlorophenyl)-5-fluoro-4-((4-methoxyphenyl)amino)-picolinate (0.146 g, 0.377 mmol) and 1,3-dichloro-5,5-dimethylimidazolidine-2,4-dione (0.149 g, 0.755 mmol) in 1:1 $CH_3CN/H_2O$ (5 mL) was added 1 M sulfuric acid ($H_2SO_4$, 0.4 mL). After heating to reflux for 1 h, analysis by liquid chromatography/mass spectrometry (LC/MS) showed that the reaction was complete. The reaction mixture was added to $CH_2Cl_2$ (20 mL). The organic layer was washed with a saturated solution of NaCl and dried ($MgSO_4$), and the solvent was removed leaving 0.242 g of an orange oil. Preparative TLC on silica gel eluting with 20% EtOAc/hexane gave methyl 4-amino-3-chloro-6-(4-chlorophenyl)-5-fluoropicolinate (47 mg, 0.142 mmol, 38% yield) as a yellow oil: $^1$H NMR (400

MHz, CDCl$_3$) δ 7.87 (m, 2H), 7.43 (m, 2H), 4.94 (br s, 2H), 3.99 (s, 3H); $^{19}$F NMR (376 MHz, CDCl$_3$) δ −140.86; ESIMS m/z 315.607 ([M]).

Example 5

Methyl 6-(4-chlorophenyl)-5-fluoro-4-((4-oxocyclo-hexa-2,5-dien-1-ylidene)amino)-picolinate

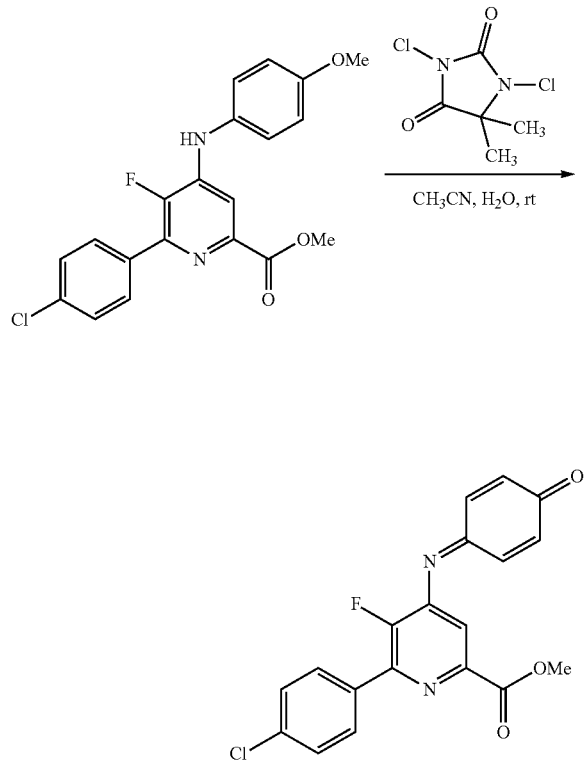

A mixture of methyl 6-(4-chlorophenyl)-5-fluoro-4-((4-methoxyphenyl)amino)-picolinate (0.155 g, 0.400 mmol) and 1,3-dichloro-5,5-dimethylimidazolidine-2,4-dione (0.158 g, 0.800 mmol) in 1:1 CH$_3$CN/H$_2$O (5 mL) was stirred at room temperature. After 30 min the suspension of the solid ester dissolved giving a yellow/orange solution, then an orange solid began to form. After stirring at room temperature for 2 h, the reaction solution was decanted, and the orange solid was washed with 1:1 CH$_3$CN/H$_2$O (10 mL). The solid was dissolved in CH$_2$Cl$_2$ and dried (MgSO$_4$), and the solvent was removed to give methyl 6-(4-chlorophenyl)-5-fluoro-4-((4-oxocyclohexa-2,5-dien-1-ylidene)amino)picolinate (0.13 g, 0.316 mmol, 79% yield) as an orange solid: mp 154-156° C.; $^1$H NMR (400 MHz, CDCl$_3$) δ 7.97 (d, J=7.3 Hz, 2H), 7.65 (d, J=5.4 Hz, 1H), 7.48 (d, J=8.6 Hz, 2H), 7.36 (dd, J=10.1, 2.6 Hz, 1H), 6.87 (d, J=10.3 Hz, 1H), 6.77 (dd, J=10.1, 2.1 Hz, 1H), 6.61 (dd, J=10.2, 2.1 Hz, 1H), 4.02 (s, 3H); $^{19}$F NMR (376 MHz, CDCl$_3$) δ −145.68.

Example 6

Methyl 4-amino-6-(4-chlorophenyl)-5-fluoropicolinate

A mixture of methyl 6-(4-chlorophenyl)-5-fluoro-4-((4-oxocyclohexa-2,5-dien-1-ylidene)amino)picolinate (0.074 g, 0.20 mmol) and 0.1 M H$_2$SO$_4$ (0.2 mL) in a 1:1 mixture of CH$_3$CN/H$_2$O (2 mL) was heated to 80° C. for 1 h. After stirring at room temperature for 2 h, the reaction mixture was added to CH$_2$Cl$_2$ (10 mL). The organic layer was washed with a saturated solution of NaCl and dried (MgSO$_4$), and the solvent was removed. Preparative TLC on silica gel eluting with 20% EtOAc/hexane gave methyl 4-amino-6-(4-chlorophenyl)-5-fluoropicolinate (0.050 g, 0.169 mmol, 85% yield) as a light yellow solid: $^1$H NMR (400 MHz, CDCl$_3$) δ 7.83 (m, 2H), 7.45 (d, J=6.2 Hz, 1H), 7.37 (m, 2H), 4.40 (br s, 2H), 3.90 (s, 3H). ESIMS m/z 279.77 ([M−H]$^-$); $^{19}$F NMR (376 MHz, CDCl$_3$) δ −145.11.

Example 7

Methyl 4-amino-3-chloro-6-(4-chlorophenyl)-5-fluoropicolinate

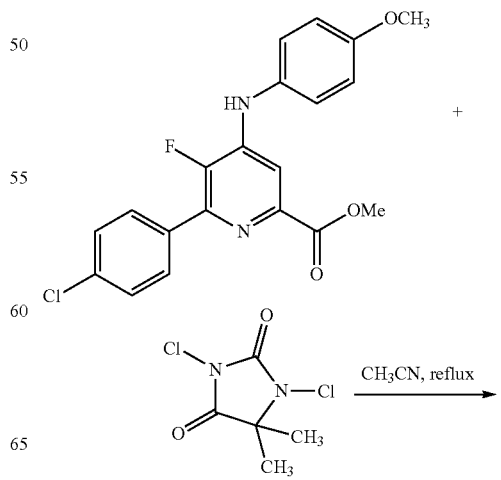

-continued

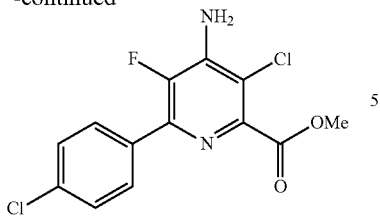

A magnetically-stirred mixture of methyl 6-(4-chlorophenyl)-5-fluoro-4-((4-methoxyphenyl)amino)-picolinate (112 mg, 0.4 mmol) and 1,3-dichloro-5,5-dimethylimidazolidine-2,4-dione (47.3 mg, 0.240 mmol) in $CH_3CN$ (5 mL) was heated to reflux for 1 h. Upon cooling to room temperature the reaction mixture was added to $EtOAc/H_2O$ (25 mL). The organic layer was washed with a saturated solution of NaCl (25 mL) and dried ($MgSO_4$), and the solvent was removed to give 0.21 g of a light oil. Preparative TLC on silica gel eluting with 40% EtOAc/hexane gave methyl 4-amino-3-chloro-6-(4-chlorophenyl)-5-fluoropicolinate (94 mg, 0.292 mmol, 73.1% yield) as an off-white solid: $^1$H NMR (400 MHz, $CDCl_3$) δ 7.88 (m, 2H), 7.44 (m, 2H), 4.92 (br s, 2H), 3.99 (s, 3H); $^{19}$F NMR (376 MHz, $CDCl_3$) δ −140.86. ESIMS m/z 315 ([M+H]$^+$).

What is claimed is:

1. A compound of Formula E

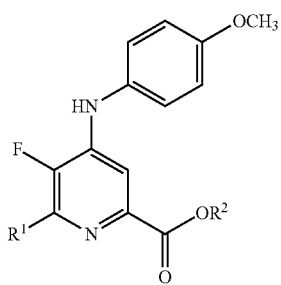

wherein $R^1$ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and $R^2$ represents $C_1$-$C_4$ alkyl.

2. A compound of Formula G

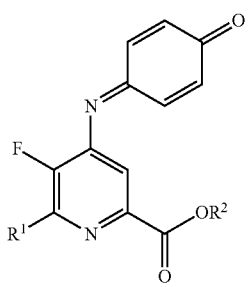

wherein $R^1$ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and $R^2$ represents $C_1$-$C_4$ alkyl.

* * * * *